United States Patent [19]

Kameda

[11] Patent Number: 4,548,908

[45] Date of Patent: Oct. 22, 1985

[54] COMPETITIVE IMMUNOFLUORESCENCE ASSAY AND TEST KIT

[75] Inventor: Naomi Kameda, Portola Valley, Calif.

[73] Assignee: Sclavo, Inc., Sunnyvale, Calif.

[21] Appl. No.: 498,864

[22] Filed: May 27, 1983

Related U.S. Application Data

[63] Continuation-in-part of Ser. No. 376,204, May 7, 1982, abandoned.

[30] Foreign Application Priority Data

May 6, 1983 [WO] PCT Int'l Appl. .................. PCT/US83/00675

[51] Int. Cl.[4] .................. G01N 33/52; G01N 33/58; B65D 71/00
[52] U.S. Cl. .................................. 436/500; 436/540; 436/800; 436/808; 436/815; 436/817; 436/826; 422/61
[58] Field of Search .................. 436/500, 536–540, 436/800, 808, 815, 817, 826; 422/61

[56] References Cited

U.S. PATENT DOCUMENTS

| | | | |
|---|---|---|---|
| 3,981,982 | 9/1976 | Oslapas et al. | 436/542 |
| 4,279,617 | 7/1981 | Masson et al. | 435/7 |
| 4,298,592 | 11/1981 | Lin | 436/542 |
| 4,339,427 | 7/1982 | Goldstein et al. | 436/538 |

FOREIGN PATENT DOCUMENTS 150547 of 1979 Japan .................................. 436/546

OTHER PUBLICATIONS

Pourfarzaneh et al., Clin. Chem. 26 (6) 730–731 (1980).
Chard et al., Clin. Chem., 25 (6) 973–976 (1979).
Cidosky et al., Analytical Chem. 51 (11) 1602–1605 (1979).
Karnes et al., Clin. Chem., 27 (1981) 249–252.
Soini et al., Clin. Chem., 25 (1979) 353–361.

*Primary Examiner*—Christine M. Nucker
*Attorney, Agent, or Firm*—Ciotti & Murashige

[57] ABSTRACT

Competitive immunofluorescence assays for antigens in which immune complexes are precipitated with a nonfluorescent, nonlight-scattering precipitant such as polyethylene glycol and the resulting immunoprecipitate is dissolved with a nonfluorescent solvent of low ionic strength that maintains the pH of the solution substantially constant for immunofluorescence intensity reading. The assays are carried out by incubating the sample with fluorescent-labeled antigen, anti-antigen antibody, and a secondary antibody to the anti-antigen antibody followed by addition of the precipitant to form an immunoprecipitate. The precipitate is separated by centrifuging, dissolved in the solvent, and the immunofluorescence intensity of the solution is read with a fluorometer and compared to a standard curve.

15 Claims, No Drawings

COMPETITIVE IMMUNOFLUORESCENCE ASSAY AND TEST KIT

CROSS-REFERENCE TO RELATED APPLICATION

This application is a continuation-in-part of copending application Ser. No. 376,204, filed May 7, 1982 now abandoned.

DESCRIPTION

1. Technical Field

The invention is in the field of immunodiagnostics. More particularly it involves an improved competitive immunofluorescence test for antigens.

2. Background Art

Competitive immunoassays for antigens or haptens are known in the immunodiagnostic art. They are based on competition for specific antibody against the antigen between labeled antigen (known) and unlabeled antigen (unknown) in the sample being assayed. Immune complexes that form between the antigen/hapten and antibody are separated and the amount of label therein detected by appropriate label detection means. Te concentration of unknown (unlabeled) antigen/hapten in the sample is determined by comparison with the effect of standards.

U.S. Pat. Nos. 3,981,982 and 4,298,592 describe a type of competitive radioimmunoassay called a "double antibody separation" assay. In this technique the sample suspected of containing antigen is first incubated with a first specific antibody and known radiolabeled antigen. Following this a second antibody that is specific to the first antibody is added together with polyethylene glycol. The second antibody and polyethylene glycol form a complex with the antigen-first antibody reaction product that agglomerates and precipitates from the incubation mixture. The precipitate is separated from the supernatant containing free antigen. The radioactivity of the separated precipitate is read directly with a scintillation counter and the concentration of antigen in the sample is determined by comparing the reading to a standard radioactivity-antigen concentration curve. These radioimmunoassays are sensitive but have the disadvantage of all radioimmunoassays of involving radioactive reagents that must be handled, used, and disposed of with extreme care by highly trained personnel. Corresponding immunofluorescence assays in which the fluorescence of a solid phase is read are known. Such assays suffer from high background fluorescence from the solid phase itself or from scattered light.

Chard, T., and Sykes, A., *Clin Chem* (1979) 26/6: 973–976 teach a fluoroimmunoassay for human choriomammotropin in which a plasma sample is incubated with fluorescein-labeled human choriomammotropin and sheep antiserum to the hormone. Following the incubation immune complexes are separated from free hormone by addition of aqueous polyethylene glycol. The mixture is centrifuged and the fluorescence of the supernatant is read and compared to a standard. Such assays in which the fluorescence of the supernatant is read have the problem of fluoresence due to interfering materials in the supernatant (plasma or serum).

Pourfarzaneh, M., et al, *Clin Chem* (1980) 26/6: 730–733, describes a competitive immunofluorescence assay for cortisol in serum. The serum sample is incubated with fluorescein-labeled cortisol and anti-cortisol antibody coupled to magnetizable cellulose/iron oxide particles. After the incubation the solid phase is separated, washed to remove free, labeled antigen, and eluted with an equivolume mixture of methanol and 0.02M NaOH. The fluorescence of the eluate is read with a fluorometer and compared to a standard curve to determine the concentration of cortisol in the sample.

Japanese Patent Application No. 150547/79 describes direct and indirect immunofluorescence assays for various antigens. The sample is first incubated with antibody (fluorochrome-labeled in the direct assay, unlabeled in the indirect assay). The mixture is then incubated with an immunoadsorbent. The indirect assay involves an additional incubation of the immunoadsorbent with a fluorochrome-labeled antibody against the first antibody. In both types of assay, immune complexes are eluted from the immunoadsorbent with 0.02–0.04N NaOH and the fluorescence of the eluate is read and compared to a standard. These prior assays involving immunoadsorption and immobilization have several shortcomings. Firstly, the reproducibility of the immobilization is often inconsistent and affects the precision of the assay adversely. The adsorption may also affect the stability of the immune complexes adversely and cause artificially low immunofluorescence intensity readings. Elution inefficiency and/or interference from spurious eluted materials may also cause artificially low fluorescence intensity readings.

In contrast to the above described prior competitive immunofluorescence assays, the invention assay does not involve solid phase readings or readings of supernatants or eluates that may contain interfering materials. Instead the invention assay involves precipitating the immune complex with a nonfluorescent, non-light scattering immunoprecipitant, dissolving the resulting immunoprecipitate with a solvent that does not add background fluorescence or light scatter, and reading the solution. Compared to the prior competitive immunofluorescence assays, the invention assay is highly sensitive and has improved reproducibility and dose-response and precision characteristics, and requires less antibody reagent.

DISCLOSURE OF THE INVENTION

One aspect of the invention is a competitive assay for determining the amount of an antigen in a sample suspected of containing the antigen comprising: (a) incubating the sample with a solution of a fluorescent-labeled antigen, anti-antigen antibody, and an antibody against the anti-antigen antibody; (b) adding a nonfluorescent nonlight-scattering immunoprecipitant to the incubation mixture to form an immunoprecipitate; (c) separating the immunoprecipitate and dissolving the immunoprecipitate in a nonfluorescent solvent that has a low ionic strength and maintains the pH of the resulting solution substantially constant; and (d) measuring the fluorescence intensity of the solution of step (c) and comparing said fluorescence intensity to a standard curve.

Another aspect of the invention is a test kit for carrying out the above-described competition immunofluorescence assay comprising in association: (a) a fluorescent-labeled antigen reagent; (b) anti-antigen antibody reagent; (c) an antibody against the anti-antigen antibody; and (d) a nonfluorescent solvent for dissolving immunoprecipitates of the immunoprecipitant that has a low ionic strength and the ability to maintain the pH of the immunoprecipitate solution substantially constant.

MODES FOR CARRYING OUT THE INVENTION

The sample that is analyzed by the invention method is a body fluid such as blood, blood serum, blood plasma, urine, lymph fluid, bile, spinal fluid or the like. The particular body fluid analyzed may vary with the antigen being assayed. In most instances blood serum will be used. About 0.1 to about 500 µl of fluid will be used per assay. Samples may be cryopreserved pending analysis if necessary.

Substances that may be assayed by the invention method include antigens (molecules that elicit an immune response when introduced into the bloodstream of a vertebrate host) and haptens that are not immunogenic per se but may be conjugated to a protein carrier to form a conjugate that is immunogenic and capable of raising antibodies against the hapten. The term "antigen" is used herein to generically denote both antigenic and haptenic compositions. Such substances include drugs, hormones, pesticides, toxins, vitamins, human, bacterial, and viral proteins, and the like. Examples of antigens that may be assayed by the invention method are thyroxine (T4), triiodothyronine (T3), digoxin, gentamicin, amikacin, tobramycin, kanamycin, netilmicin, cortisol, luteinizing hormone, digitoxin, vitamin B12, progesterone, human chorionic gonadotropin, theophylline, angiotensin, human growth hormone, and the like.

The reagents that are incubated with the sample suspected of containing antigen to form immune complexes are (1) fluorescent-labeled antigen, (2) anti-antigen antibody, (3) antibody against the anti-antigen antibody, and (4) a nonfluorescent non-light-scattering immunoprecipitant. The fluorescent-labeled antigen may be made by coupling the antigen with a reactive derivative of a fluorogen such as fluorescein (eg, fluorescein isothiocyanate (FITC) and fluorescein amine), rhodamine or dansyl using multifunctional coupling agents such as aldehydes, carbodiimides, dimaleimides, imidates, and succinimides. Fluorescein is a preferred label. Antibody against the antigen may be made by inoculating a host vertebrate with the antigen, typically repeatedly at several day intervals, bleeding the host and separating Ig from the blood. Antibody against the antibody to the antigen may be made by immunizing another host vertebrate species with said Ig and collecting Ig from the second host. The nonfluorescent, nonlight-scattering immunoprecipitant is a compound that causes an immune complex to precipitate or increases the rate of immune complex precipitation. Compounds that are conventionally used to precipitate proteins and that have the required nonfluorogenic properties may be used. Examples of such materials are polyethylene glycol having a molecular weight in the range of about 3000 to about 12000, preferably about 4000 to 10000, and inorganic salts such as ammonium sulfate. Polyethylene glycol is a preferred immunoprecipitant.

The absolute amounts of the reagents used will, of course, depend upon the volume of the sample. A known amount of labeled antigen will be used. The labeled antigen may be diluted to provide a reagent that is stoichiometrially ideal for the antiserum used. Common aqueous buffers such as Tris (an aqueous solution of tris(hydroxymethyl)amino methane), barbital, borate, phosphate, and the like may be used to dilute the labeled antigen. The antiserum against the antigen will normally be added in excess of the total amount of antigen in the reaction medium. It, too, may be diluted with an aqueous buffer. The second antiserum will be also added in excess relative to the antiserum against the antigen. The second antiserum should be one that does not cross react with the antigen. The immunoprecipitant will normally be added as a dilute aqueous solution (about 5% to 8% by weight) in amounts in the range of about 2% to about 20%, preferably 5% to about 8% by weight of solution based on the second antiserum.

The sequence in which the reagents are added to the sample is generally not critical. Usually the labeled antigen, first antiserum, and second antiserum will be incubated with the sample separately and the immunoprecipitant added later. The incubation will be carried out at a temperature and pH that permits formation of immune complexes. Moderate temperatures in the range of about 15° C. to about 55° C., conveniently room temperature, and pHs in the range of about 6 and 9, preferably 7 to 8, will normally be used. The duration of the incubation will depend to some extent upon the sequence in which the reagents are added to the sample. In the case where the labeled antigen and two antisera are added together at the above conditions, incubation times of about one min to two days will be sufficient time to allow the antigen and antisera to react and form immune complexes. The complexes formed by the antigen (labeled and unlabeled in the sample) and the two antisera remain in solution and may not agglomerate and precipitate until the immunoprecipitant is added. In instances where the immunoprecipitant is included in the incubation, immunoprecipitation occurs concurrently with the formation of the immune complexes. When immunoprecipitation is carried out in a separate step by adding the precipitant later, about one min to one hr are allowed for the precipitant to be incorporated into the complex and form a precipitate.

Following the immunoprecipitation, the precipitate is separated from the supernatant, such as by centrifuging, and the supernatant is discarded. The precipitate may be washed with buffer if desired. The precipitate is then dissolved in a nonfluorescent solvent that has a low ionic strength (ie, typically less than about 0.2 and more usually between about 0.001 and 0.06) and that maintains the pH of the resulting solution substantially constant (ie, ±0.005). Preferably the pH is maintained above 8, more preferably above 9. Examples of such solvents are aqueous solutions of alkali metal (eg, Na, K) hydroxides and borates, barbital, and Tris. Preferably the solvent has the capacity to buffer the solution at the specified pH. The ionic strength that provides maximum fluorescence intensity will vary depending upon the particular solvent involved. For instance, in the case of sodium hydroxide the ionic strength is less than about 0.04, usually 0.02 to 0.04, and preferably approximately 0.03. For sodium borate the ionic strength should be less than about 0.2, usually 0.01 to 0.1, and preferably approximately 0.06. A minimum volume of the solvent (ie, that amount that just dissolves the precipitate) is preferably used. That amount will usually range between about 100 and 500 µl for samples of the above described volumes. The dissolution may be done at moderate temperatures, conveniently at ambient temperature. The resulting solution is then transferred to an appropriate container, eg, a flow cell, for fluorescence intensity reading. The fluorescence intensity is compared to a standard curve of fluorescence intensity vs antigen concentration derived by assaying a series of samples containing known amounts of antigen. From this comparison, the quantity of antigen in the sample is determined.

The basic ingredients of the test kit for carrying out the invention assay are: (1) the fluorescent-labeled antigen, (2) the first antiserum against the antigen, (3) the antiserum against the first antiserum, (4) the immunoprecipitant, and (5) the solvent. These ingredients are preferably packaged separately in the kit and will typically be provided in amounts sufficient to carry out multiple assays. The test kit may also include appropriate buffers, unlabeled antigen reagent for preparing standard and control samples, equipment or vials for performing the assay, and instructions for carrying out the assay. The kit components may be packaged in manners conventionally used in diagnostic kit manufacturing. The kits will be stored at reduced temperatures, preferably 2° C. to 6° C.

The following examples further illustrate the invention and its advantages over alternative assay techniques. These examples are not intended to limit the invention in any manner. Unless indicated otherwise, percentages are by weight.

EXAMPLE 1

T4 Assay by Invention Method and Prior Art

Twenty-five μl aliquots of serum containing known amounts of T4 were each incubated at 25° C. for 20 min with 25 μl of FITC-labeled T4 in carbonate buffer, 0.01M, pH 8.6, 25 μl of a mixture of rabbit anti-T4 serum and goat anti-rabbit Ig serum in phosphate buffered saline. Following incubation, one μl of a cold 6.5% aqueous solution of polyethylene glycol (8000 mw) was added to the mixture. The resulting precipitates were separated by centrifugation and the supernatants were discarded. The precipitates were each dissolved in 200 μl of 0.03N aqueous NaOH. The solutions were transferred to flow cell cuvettes and their fluorescence intensities were read with a fluorometer.

A duplicate set of T4-containing aliquots were assayed by the procedure of Example 1 of Japanese Patent Application No. 150547/79.

The results of both assays are reported in Table 1 below.

TABLE 1

| T4/Tube (ng) | Relative Fluorescence Intensity (RFI) Normalized for Comparison | |
|---|---|---|
| | Prior Art | Invention |
| 0 | 45 | 340 |
| | 46 | 342 |
| 1.25 | 42 | 278 |
| | 41 | 282 |
| 2.50 | 31 | 217 |
| | 34 | 217 |
| 7.25 | 34 | 151 |
| | 28 | 141 |

As indicated by the data of Table 1, the effective assay range in RFI is about ten-fold greater in the invention method relative to the prior art method. The coefficient of variation in RFI for the invention method was less than 2% as compared to about 10% for the prior art method. This indicates that the precision of the invention T4 assay is substantially better than the precision of the comparison prior art T4 assay.

EXAMPLE 2

T3 Assay

T3 assays were carried out on standards and unknowns using the general procedure described in Example 1. The reagents and incubation conditions were:

| Item | Description |
|---|---|
| Serum sample size | 100 μl |
| FITC-labeled T3 reagent | 25 μl |
| rabbit anti-T3 antibody-goat anti-rabbit Ig antibody | 25 μl |
| incubation temp | 37° C. |
| incubation time | 1 hr |

The results of these assays are reported in Table 2 below.

TABLE 2

| | | Concentration (ng %) | |
|---|---|---|---|
| Standard/Sample | RFI | Obtained | Actual |
| 1. Standard 1 | 731 | — | 0.0 |
| 2. Standard 1 | 762 | — | 0.0 |
| 3. Standard 2 | 712 | — | 50 |
| 4. Standard 2 | 713 | — | 50 |
| 5. Standard 3 | 684 | — | 100 |
| 6. Standard 3 | 697 | — | 100 |
| 7. Standard 4 | 583 | — | 400 |
| 8. Standard 4 | 601 | — | 400 |
| 9. Standard 5 | 528 | — | 800 |
| 10. Standard 5 | 526 | — | 800 |
| 11. Sample a | 705 | 68 | 62 |
| 12. Sample a | 712 | 52 | 62 |
| 13. Sample b | 678 | 132 | 172 |
| 14. Sample b | 672 | 143 | 172 |
| 15. Sample c | 569 | 523 | 486 |
| 16. Sample c | 574 | 470 | 486 |

EXAMPLE 3

Digoxin Assay

Digoxin assays were carried out on standards and unknowns using the general procedure described in Example 1. The reagents and incubation conditions were:

| Item | Description |
|---|---|
| Sample size | 100 μl |
| FITC-labeled digoxin reagent | 25 μl |
| rabbit anti-digoxin antibody-goat anti-rabbit Ig antibody | 25 μl |
| incubation temp | 37° C. |
| incubation time | 1 hr |

The results of these assays are reported in Table 3 below.

TABLE 3

| | | Concentration (ng/ml) | |
|---|---|---|---|
| Standard/Sample | RFI | Obtained | Actual |
| 1. Standard 1 | 2920 | — | 0.0 |
| 2. Standard 1 | 2937 | — | 0.0 |
| 3. Standard 2 | 2736 | — | 1.0 |
| 4. Standard 2 | 2801 | — | 1.0 |
| 5. Standard 3 | 2463 | — | 2.0 |
| 6. Standard 3 | 2543 | — | 2.0 |
| 7. Standard 4 | 1979 | — | 4.0 |
| 8. Standard 4 | 2020 | — | 4.0 |
| 9. Standard 5 | 1803 | — | 8.0 |
| 10. Standard 5 | 1792 | — | 8.0 |
| 11. Sample a | 1821 | 7.05 | 6.7 |

TABLE 3-continued

| Standard/Sample | RFI | Concentration (ng/ml) Obtained | Actual |
|---|---|---|---|
| 12. Sample a | 1833 | 6.6 | 6.7 |
| 13. Sample b | 2532 | 1.90 | 2.0 |
| 14. Sample b | 2541 | 1.86 | 2.0 |
| 15. Sample c | 1922 | 4.82 | 5.1 |
| 16. Sample c | 1910 | 5.00 | 5.1 |

EXAMPLE 4

Gentamicin Assay

Gentamicin assays were carried out on standards and unknowns using the general procedure described in Example 1. The reagents and incubation conditions were:

| Item | Description |
|---|---|
| sample size | 25 μl |
| FITC-labeled reagent | 10 μl |
| rabbit anti-gentamicin antibody- goat anti-rabbit Ig antibody | 25 μl |
| incubation temp | 25° C. |
| incubation time | 10 min |

The results of these assays are reported in Table 4 below.

TABLE 4

| Standard/Sample | RFI | Concentration (μg/ml) Obtained | Actual |
|---|---|---|---|
| 1. Standard 0 | 7086 | — | 0.0 |
| 2. Standard 1 | 6793 | — | 0.5 |
| 3. Standard 2 | 4453 | — | 2.0 |
| 4. Standard 3 | 2822 | — | 4.0 |
| 5. Standard 4 | 1234 | — | 16.0 |
| 6. Sample 1 | 1902 | 7.9 | 8.0 |
| 7. Sample 2 | 2791 | 4.15 | 4.0 |
| 8. Sample 3 | 1200 | 17.0 | 16.0 |
| 9. Sample 4 | 1853 | 8.2 | 8.0 |
| 10. Sample 5 | 6480 | 0.66 | 0.5 |
| 11. Sample 6 | 3828 | 2.45 | 2.0 |
| 12. Sample 7 | 5814 | 0.99 | 1.0 |
| 13. Sample 8 | 6921 | 0.5 | 0.0 |
| 14. Sample 9 | 5666 | 1.08 | 1.0 |
| 15. Sample 7 | 5800 | 1.00 | 1.0 |
| 16. Sample 7 | 5821 | 0.99 | 1.0 |
| 17. Sample 7 | 5762 | 1.03 | 1.0 |
| 18. Sample 7 | 5748 | 1.03 | 1.0 |
| 19. Sample 7 | 5819 | 0.99 | 1.0 |
| 20. Sample 7 | 5709 | 1.05 | 1.0 |
| 21. Sample 7 | 5798 | 1.00 | 1.0 |
| 22. Sample 7 | 5810 | 0.99 | 1.0 |
| 23. Sample 4 | 1870 | 8.1 | 8.0 |
| 24. Sample 4 | 1854 | 8.2 | 8.0 |
| 25. Sample 4 | 1900 | 7.9 | 8.0 |
| 26. Sample 4 | 1888 | 8.0 | 8.0 |
| 27. Sample 4 | 1909 | 7.9 | 8.0 |
| 28. Sample 4 | 1844 | 8.3 | 8.0 |
| 29. Sample 4 | 1865 | 8.2 | 8.0 |
| 30. Sample 4 | 1866 | 8.2 | 8.0 |

EXAMPLE 5

Amikacin Assay

Amikacin assays were carried out on standards and unknowns using the general procedure described in Example 1. The reagents and incubation conditions were:

| Item | Description |
|---|---|
| Serum sample size | 25 μl |
| FITC-labeled amikacin | 10 μl |
| rabbit anti-amikacin antibody- goat anti-rabbit Ig antibody | 25 μl |
| incubation temp | 25° C. |
| incubation time | 10 min |

The results of these assays are reported in Table 5 below.

TABLE 5

| Standard/Sample | RFI | Concentration (μg/ml) Obtained | Actual |
|---|---|---|---|
| 1. Standard 1 | 2815 | — | 0.0 |
| 2. Standard 2 | 2128 | — | 3.0 |
| 3. Standard 3 | 1644 | — | 10.0 |
| 4. Standard 4 | 1357 | — | 20.0 |
| 5. Standard 5 | 1011 | — | 50.0 |
| 6. Sample 1 | 1640 | 10.1 | 10.0 |
| 7. Sample 2 | 1142 | 36.0 | 35.0 |
| 8. Sample 3 | 2562 | 3.0 | 0.0 |
| 9. Sample 4 | 1008 | 51.0 | 50.0 |
| 10. Sample 5 | 1180 | 32.5 | 35.0 |
| 11. Sample 6 | 2169 | 2.7 | 3.0 |
| 12. Sample 7 | 1400 | 18.7 | 20.0 |
| 13. Sample 2 | 1150 | 35.2 | 35.2 |
| 14. Sample 2 | 1161 | 34.3 | 35.0 |
| 15. Sample 2 | 1154 | 35.1 | 35.0 |
| 16. Sample 2 | 1205 | 38.0 | 35.0 |
| 17. Sample 2 | 1172 | 33.3 | 35.0 |
| 18. Sample 2 | 1131 | 37.0 | 35.0 |
| 19. Sample 2 | 1141 | 36.0 | 35.0 |
| 20. Sample 2 | 1139 | 36.0 | 35.0 |
| 21. Sample 1 | 1652 | 9.9 | 10.0 |
| 22. Sample 1 | 1639 | 10.1 | 10.0 |
| 23. Sample 1 | 1639 | 10.0 | 10.0 |
| 24. Sample 1 | 1646 | 10.0 | 10.0 |
| 25. Sample 1 | 1661 | 9.7 | 10.0 |
| 26. Sample 1 | 1632 | 10.3 | 10.0 |
| 27. Sample 1 | 1642 | 10.0 | 10.0 |
| 28. Sample 1 | 1658 | 9.8 | 10.0 |
| 29. Sample 1 | 1640 | 10.1 | 10.0 |

EXAMPLE 6

Tobramycin Assay

Tobramycin assays were carried out on standards and unknowns using the general procedure of Example 1. The reagents and incubation conditions were:

| Item | Description |
|---|---|
| Sample size | 25 μl |
| FITC-labeled reagent | 10 μl |
| rabbit anti-tabramycin antibody- goat anti-rabbit Ig antibody | 25 μl |
| incubation temp | 25° C. |
| incubation time | 10 min |

The results of these assays are reported in Table 6 below.

TABLE 6

| Standard/Sample | RFI | Concentration (μg/ml) Obtained | Actual |
|---|---|---|---|
| 1. Standard 0 | 1957 | — | 0.0 |
| 2. Standard 1 | 1882 | — | 0.5 |
| 3. Standard 2 | 1502 | — | 2.0 |
| 4. Standard 3 | 1057 | — | 4.0 |
| 5. Standard 4 | 610 | — | 16.0 |
| 6. Sample 1 | 801 | 8.00 | 8.0 |
| 7. Sample 2 | 1752 | 0.99 | 1.0 |
| 8. Sample 3 | 621 | 15.70 | 16.0 |

TABLE 6-continued

| Standard/Sample | RFI | Concentration (μg/ml) | |
|---|---|---|---|
| | | Obtained | Actual |
| 9. Sample 4 | 782 | 8.40 | 8.0 |
| 10. Sample 5 | 1872 | 0.55 | 0.5 |
| 11. Sample 6 | 1733 | 1.07 | 1.0 |
| 12. Sample 7 | 1452 | 2.22 | 2.0 |
| 13. Sample 8 | 1095 | 3.73 | 4.0 |
| 14. Sample 9 | 1949 | 0.5 | 0.0 |
| 15. Sample 2 | 1748 | 1.00 | 1.0 |
| 16. Sample 2 | 1753 | 0.99 | 1.0 |
| 17. Sample 2 | 1740 | 1.03 | 1.0 |
| 18. Sample 2 | 1739 | 1.03 | 1.0 |
| 19. Sample 2 | 1751 | 0.99 | 1.0 |
| 20. Sample 2 | 1745 | 1.01 | 1.0 |
| 21. Sample 2 | 1748 | 1.00 | 1.0 |
| 22. Sample 2 | 1749 | 1.00 | 1.0 |
| 23. Sample 1 | 799 | 8.0 | 8.0 |
| 24. Sample 1 | 820 | 7.4 | 8.0 |
| 25. Sample 1 | 819 | 7.4 | 8.0 |
| 26. Sample 1 | 806 | 7.9 | 8.0 |
| 27. Sample 1 | 788 | 8.3 | 8.0 |
| 28. Sample 1 | 793 | 8.1 | 8.0 |
| 29. Sample 1 | 825 | 7.3 | 8.0 |
| 30. Sample 1 | 800 | 8.0 | 8.0 |

EXAMPLE 7

Tobramycin Assay using Sodium Borate

Tobramycin assays were carried out on standards using the procedure of Example 6 except that 0.03M sodium borate was used as a solvent instead of 0.03N Sodium hydroxide. Eight hundred μl of the borate solution was used for each precipitate. For comparison purposes assays using 0.03N sodium hydroxide were also carried out. The results of these assays are reported in Table 7 below.

TABLE 7

| Standard | Concentration μg/ml | RFI NaOH | Borate |
|---|---|---|---|
| 1 | 0 | 2500 | 3094 |
| 2 | 1.0 | 2230 | 2513 |
| 3 | 2.0 | 1950 | 1653 |
| 4 | 4.0 | 1360 | 1519 |
| 5 | 8.0 | 990 | 1106 |
| 6 | 16.0 | 760 | 793 |

EXAMPLE 8

The usefulness of the sodium borate solution of Example 7 as a solvent in assays of T4 and gentamicin was shown as follows. Known amounts of FITC-labeled antigen in the carbonate buffer of Example 1 were incubated with rabbit serum against the antigen and goat anti-rabbit serum as in Example 1. The labeled T4 solution contained 0.82 ng T4 whereas the labeled gentamicin solution contained 0.5 ng gentamicin. The resulting immune complexes were precipitated with aqueous polyethylene glycol, the precipitates were separated, and the supernatants were discarded as in Example 1. The resulting precipitates were dissolved in 0.03N sodium hydroxide or 0.03M sodium borate and the fluorescence intensities were read with a fluorometer. These tests were run in duplicate and are reported below.

| Antigen | NaOH | Borate |
|---|---|---|
| T4 | 1658 | 1835 |
| | 1690 | 1882 |
| Gentamicin | 1962 | 2377 |
| | 1973 | 2418 |

Modifications of the above described modes for carrying out the invention that are obvious to those of ordinary skill in the immunodiagnostics art and/or related arts are intended to be within the scope of the following claims.

I claim:

1. A competitive immunofluorescence assay for determining the amount of an antigen in a sample suspected of containing the antigen comprising:
   (a) incubating the sample with a solution of a fluorescent-labeled antigen, anti-antigen antibody, and an antibody against the anti-antigen antibody;
   (b) adding polyethylene glycol to the incubation mixture in amount effective to form an immunoprecipitate;
   (c) separating the immunoprecipitate and dissolving the immunoprecipitate in a nonfluorescent solvent that has a low ionic strength and maintains the pH of the resulting solution substantially constant; and
   (d) measuring the fluorescence intensity of the solution of step (c) and comparing said fluorescence intensity to a standard curve.

2. The competitive immunofluorescence assay of claim 1 wherein the antigen is $T_3$, $T_4$, digoxin, gentamicin, amikacin, tobramycin, kanamycin, netilmicin, or theophylline.

3. The immunofluorescence assay of claim 1 wherein the fluorescent-labeled antigen is a fluorescein-labeled antigen.

4. The competitive immunofluorescence assay of claim 1 wherein the solvent maintains the pH of the solution above about 8.

5. The competitive immunofluorescence assay of claim 1 wherein the solvent is a buffer.

6. The competitive immunofluorescence assay of claim 1 wherein the solvent is an aqueous solution of an alkali metal hydroxide or an alkali metal borate.

7. The competitive immunofluorescence assay of claim 1 wherein the solvent is aqueous sodium hydroxide having an ionic strength less than about 0.04.

8. The competitive immunofluorescence assay of claim 7 wherein the ionic strength is approximately 0.03.

9. The competitive immunofluorescence assay of claim 1 wherein the solvent is an aqueous solution of sodium borate having an ionic strength less than about 0.2.

10. The competitive immunofluorescence assay of claim 1 wherein a minimum volume of the solvent is used to dissolve the immunoprecipitate.

11. The competitive immunofluorescence assay of claim 2 wherein the fluorescent labeled antigen is fluorescein isothiocyanate labeled antigen, the solvent is aqueous sodium hydroxide having an ionic strength less than about 0.04 or sodium borate having an ionic strength less than about 0.2, said pH is above 8.

12. A test kit for carrying out the assay of claim 1, comprising:
   (a) a container containing a fluorescent-labeled antigen reagent;
   (b) a container containing anti-antigen antibody reagent;

(c) a container containing an antibody against the anti-antigen antibody;

(d) a container containing a polyethylene glycol; and (e) a container containing a nonfluorescent solvent for dissolving immunoprecipitates of the immunoprecipitant that has a low ionic strength and the ability to maintain the pH of the immunoprecipate solution substantially constant.

13. The test kit of claim 12 wherein the solvent has the ability to maintain said pH above about 8.

14. The test kit of claim 13 wherein the solvent is aqueous sodium hydroxide having an ionic strength less than about 0.04 or an aqueous solution of sodium borate having an ionic strength less than about 0.2.

15. The test kit of claim 14 wherein the fluorescent-labeled antigen is a fluorescein-labeled antigen.

* * * * *